(12) United States Patent
Begg

(10) Patent No.: US 12,303,109 B2
(45) Date of Patent: May 20, 2025

(54) SURGICAL SYSTEMS AND METHODS FOR COMPONENT COOLING WHILE WARMING FLUID TO BE INTRODUCED DURING A SURGICAL PROCEDURE

(71) Applicant: Covidien LP, Mansfield, MA (US)

(72) Inventor: Nikolai D. Begg, Wellesley, MA (US)

(73) Assignee: Covidien LP, Mansfield, MA (US)

( * ) Notice: Subject to any disclaimer, the term of this patent is extended or adjusted under 35 U.S.C. 154(b) by 77 days.

(21) Appl. No.: 17/558,854

(22) Filed: Dec. 22, 2021

(65) Prior Publication Data
US 2023/0190087 A1 Jun. 22, 2023

(51) Int. Cl.
| | |
|---|---|
| *A61B 1/12* | (2006.01) |
| *A61B 1/015* | (2006.01) |
| *A61B 1/018* | (2006.01) |
| *A61B 17/00* | (2006.01) |
| *A61B 17/32* | (2006.01) |

(52) U.S. Cl.
CPC .............. *A61B 1/128* (2013.01); *A61B 1/015* (2013.01); *A61B 1/018* (2013.01); *A61B 17/32002* (2013.01); *A61B 2017/0034* (2013.01)

(58) Field of Classification Search
CPC ......... A61B 1/128; A61B 1/015; A61B 1/018; A61B 17/32002; A61B 2017/0034; A61B 18/04; A61B 18/02; A61B 2018/00053; A61B 1/12; A61F 7/0085
See application file for complete search history.

(56) References Cited

U.S. PATENT DOCUMENTS

| | | |
|---|---|---|
| 1,585,934 A | 5/1926 | Muir |
| 1,666,332 A | 4/1928 | Hirsch |
| 1,831,786 A | 11/1931 | Duncan |
| 2,708,437 A | 5/1955 | Hutchins |

(Continued)

FOREIGN PATENT DOCUMENTS

WO WO-2022234448 A1 * 11/2022 .............. A61B 1/015

OTHER PUBLICATIONS

PCT/IB2022/062236, The International Search Report and the Written Opinion of the International Searching Authority, 13 pages, Feb. 20, 2023.

*Primary Examiner* — John P Leubecker
*Assistant Examiner* — Li-Ting Song
(74) *Attorney, Agent, or Firm* — Carter, DeLuca & Farrell LLP

(57) ABSTRACT

A surgical system includes a fluid-delivery device configured to deliver fluid to a surgical site, a surgical instrument including a heat-generating component, and a fluid inflow path defined from a fluid source to the fluid-delivery device to provide fluid to the fluid-delivery device for delivery to the surgical site. At least a portion of the fluid inflow path is thermally coupled to the heat-generating component to simultaneously draw heat from the heat-generating component and warm fluid flowing through the fluid inflow path. A method of surgery includes using a surgical instrument having a heat-generating component that generates heat during use, and introducing fluid along a fluid inflow path from a fluid source to a surgical site. At least a portion of the fluid inflow path is thermally coupled to the heat-generating component to simultaneously draw heat from the heat-generating component and warm the fluid introduced along the fluid inflow path.

19 Claims, 6 Drawing Sheets

(56) References Cited

U.S. PATENT DOCUMENTS

| | | |
|---|---|---|
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,184,256 A * | 1/1980 | Loge .................... B25F 5/008 433/104 |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,971,034 A | 11/1990 | Doi et al. |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,167,619 A | 12/1992 | Wuchinich |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle et al. |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,586,973 A | 12/1996 | Lemaire et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser et al. |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman et al. |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,871,493 A * | 2/1999 | Sjostrom ............... H01H 36/00 606/180 |

(56) References Cited

U.S. PATENT DOCUMENTS

| | | |
|---|---|---|
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,171,300 B1 * | 1/2001 | Adams ............. A61B 17/32002 433/104 |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,025,656 B2 | 9/2011 | Gruber et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,465,421 B2 | 6/2013 | Finkman et al. |
| 8,523,852 B2 | 9/2013 | Manwaring et al. |
| 8,528,563 B2 | 9/2013 | Gruber |
| 8,574,253 B2 | 11/2013 | Gruber et al. |
| 8,617,151 B2 | 12/2013 | Denis et al. |
| 8,647,349 B2 | 2/2014 | Gruber et al. |
| 8,663,264 B2 | 3/2014 | Cesarini et al. |
| 8,678,999 B2 | 3/2014 | Isaacson |
| 8,834,487 B2 | 9/2014 | Gruber et al. |
| 8,840,625 B2 | 9/2014 | Adams et al. |
| 8,840,626 B2 | 9/2014 | Adams et al. |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,760 B2 | 6/2015 | Sullivan et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,095,366 B2 | 8/2015 | Sullivan et al. |
| 9,125,550 B2 | 9/2015 | Shener-Irmakoglu et al. |
| 9,155,454 B2 | 10/2015 | Sahney et al. |
| 9,259,233 B2 | 2/2016 | Gruber et al. |
| 9,649,123 B2 * | 5/2017 | Riva ................. A61B 17/1622 |
| 9,955,991 B2 * | 5/2018 | Riva ................. A61B 17/32002 |
| 10,178,997 B2 * | 1/2019 | Edwards ............ A61B 17/1622 |
| 10,898,218 B2 * | 1/2021 | Prokop ............. A61B 17/32002 |
| 11,065,147 B2 | 7/2021 | Prokop et al. |
| 2001/0039963 A1 | 11/2001 | Spear et al. |
| 2001/0047183 A1 | 11/2001 | Privitera et al. |
| 2002/0040229 A1 * | 4/2002 | Norman ........... A61B 17/32002 606/180 |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1 | 3/2006 | Shener |
| 2006/0047239 A1 | 3/2006 | Nita et al. |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0208233 A1 * | 8/2008 | Barnes ................ A61F 9/00763 606/171 |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0034943 A1 | 2/2011 | Churchill et al. |
| 2011/0077674 A1 | 3/2011 | Sullivan et al. |
| 2011/0118544 A1 | 5/2011 | Adams et al. |
| 2011/0166419 A1 | 7/2011 | Reif et al. |
| 2012/0067352 A1 | 3/2012 | Gruber et al. |
| 2012/0078038 A1 | 3/2012 | Sahney et al. |
| 2013/0131452 A1 | 5/2013 | Kuroda et al. |
| 2014/0031834 A1 * | 1/2014 | Germain ............. A61B 1/018 606/119 |
| 2015/0051598 A1 | 2/2015 | Orszulak et al. |

(56) References Cited

U.S. PATENT DOCUMENTS

2015/0157352 A1\* 6/2015 Thistle ............. A61B 17/32002
  606/170
2017/0055810 A1\* 3/2017 Germain ........... A61M 5/16827
2020/0121496 A1\* 4/2020 Prokop .............. A61B 18/1445

\* cited by examiner

SURGICAL SYSTEMS AND METHODS FOR COMPONENT COOLING WHILE WARMING FLUID TO BE INTRODUCED DURING A SURGICAL PROCEDURE

BACKGROUND

Technical Field

The present disclosure relates generally to surgical systems and methods. More particularly, the present disclosure relates to surgical systems and methods facilitating cooling one or more components of a surgical instrument while warming fluid to be introduced into a patient during a surgical procedure.

Background of Related Art

Many surgical procedures utilize surgical instruments that have components that generate heat during use such as, for example, motors, generators, battery packs, etc. These heat-generating components need to be maintained at appropriate operating temperatures to ensure safety and adequate performance.

Many surgical procedures also require or are facilitated by the use of fluid introduced into and removed from a patient during the surgical procedure. For example, an intrauterine surgical procedure may be performed by inserting an endoscope into the uterus and introducing a fluid (for example, saline, sorbitol, or glycine) through the endoscope and into the uterus to distend the uterus. A surgical instrument such as, for example, a motor-drive tissue shaver, may be inserted through the endoscope and into the uterus to perform a surgical procedure therein such as, for example, tissue cutting and removal. The inflow and outflow of fluid during the procedure maintains the uterus in a distended state and flushes tissue and other debris from within the uterus to maintain a visible working space. In such surgical procedures, it may be desirable to pre-heat the fluid introduced into the patient. Pre-heating the fluid may be advantageous, for example, in order to make the introduction of fluid into the patient more palatable by reducing or eliminating the temperature differential between the fluid and the patient.

SUMMARY

As used herein, the term "distal" refers to the portion that is described which is farther from the operator (whether a human surgeon or a surgical robot), while the term "proximal" refers to the portion that is described which is closer to the operator. Further, to the extent consistent, any or all of the aspects described herein may be used in conjunction with any or all of the other aspects described herein.

Provided in accordance with aspects of the present disclosure is a surgical system including a fluid-delivery device configured to deliver fluid to a surgical site, a surgical instrument including a heat-generating component, and a fluid inflow path defined from a fluid source to the fluid-delivery device to provide fluid to the fluid-delivery device for delivery to the surgical site. At least a portion of the fluid inflow path is thermally coupled to the heat-generating component of the surgical instrument to simultaneously draw heat from the heat-generating component and warm fluid flowing through the fluid inflow path.

In an aspect of the present disclosure, the fluid-delivery device is an endoscope. In such aspects, the endoscope may be configured to receive a portion of the surgical instrument therethrough.

In another aspect of the present disclosure, the surgical instrument is a tissue shaver. In such aspects, the heat-generating component may be a motor configured to drive a cutting shaft of the tissue shaver.

In yet another aspect of the present disclosure, the surgical instrument includes a handpiece and an end effector assembly releasably engaged with the handpiece. In such aspects, an inflow lumen extending through the handpiece and thermally coupled to the heat-generating component may define a portion of the fluid inflow path. Alternatively or additionally, tubing engaged to the handpiece and thermally coupled to the heat-generating component may define a portion of the fluid inflow path.

In still another aspect of the present disclosure, the at least a portion of the fluid inflow path is thermally coupled to the heat-generating component of the surgical instrument via sufficient approximation of the fluid inflow path with the heat-generating component.

In still yet another aspect of the present disclosure, the at least a portion of the fluid inflow path is thermally coupled to the heat-generating component of the surgical instrument via a thermally conductive material connecting the fluid inflow path with the heat-generating component.

A method of surgery provided in accordance with aspects of the present disclosure includes using a surgical instrument having a heat-generating component that generates heat during the use of the surgical instrument, and introducing fluid along a fluid inflow path from a fluid source to a surgical site. At least a portion of the fluid inflow path is thermally coupled to the heat-generating component of the surgical instrument to simultaneously draw heat from the heat-generating component and warm the fluid introduced along the fluid inflow path.

In an aspect of the present disclosure, using the surgical instrument includes inserting a portion of the surgical instrument into the surgical site. In such aspects, using the surgical instrument may further include activating the surgical instrument to perform a surgical task at the surgical site. In some aspects, the surgical task includes tissue cutting and removal, and activating the surgical instrument includes activating a motor to drive a cutting shaft of the surgical instrument. Further, the motor may be the heat-generating component.

In another aspect of the present disclosure, the method further includes inserting an endoscope into the surgical site. Introducing the fluid along the fluid inflow path from the fluid source to the surgical site includes introducing the fluid through the endoscope.

In still another aspect of the present disclosure, using the surgical instrument includes inserting a portion of the surgical instrument through the endoscope (or other fluid delivery device) and into the surgical site.

In yet another aspect of the present disclosure, introducing the fluid along the fluid inflow path from the fluid source to the surgical site includes introducing the fluid through tubing engaged with the surgical instrument to thereby thermally couple the fluid inflow path with the heat-generating component.

In still yet another aspect of the present disclosure, introducing the fluid along the fluid inflow path from the fluid source to the surgical site includes introducing the fluid through an internal lumen defined within the surgical instrument to thereby thermally couple the fluid inflow path with the heat-generating component.

In another aspect of the present disclosure, the fluid inflow path is thermally coupled to the heat-generating component via at least one of: sufficient approximation of the fluid inflow path with the heat-generating component; or a thermally conductive material connecting the fluid inflow path with the heat-generating component.

BRIEF DESCRIPTION OF THE DRAWINGS

Various aspects and features of the present disclosure are described hereinbelow with reference to the drawings wherein like numerals designate identical or corresponding elements in each of the several views and.

DETAILED DESCRIPTION

The present disclosure provides surgical systems and methods facilitating cooling of one or more heat-generating components of a surgical instrument used during a surgical procedure while also warming fluid to be introduced into a patient during the surgical procedure. More specifically, in accordance with the system and methods of the present disclosure, inflow fluid to be introduced into a patient during a surgical procedure is utilized as a heat sink to draw heat away (and absorb the heat) from one or more heat-generating components of a surgical instrument used in the surgical procedure. This results in the dual benefit of cooling the heat-generating component(s) of the surgical instrument (by drawing the heat therefrom) while simultaneously warming the inflow fluid to be introduced into the patient (by absorbing the heat). Although described hereinbelow with respect to a surgical system including a motor-powered tissue shaver and hysteroscopic fluid management system, the aspects and features of the present disclosure are equally applicable for use with other surgical instruments (and/or for cooling other heat-generating components thereof, e.g., generators, battery packs, controllers, etc.) and/or other surgical fluid management systems. Further, the systems and methods detailed herein are not limited to use with human-operated surgical instrumentation but, rather, also apply to surgical robotics implementations.

Figure 1A:
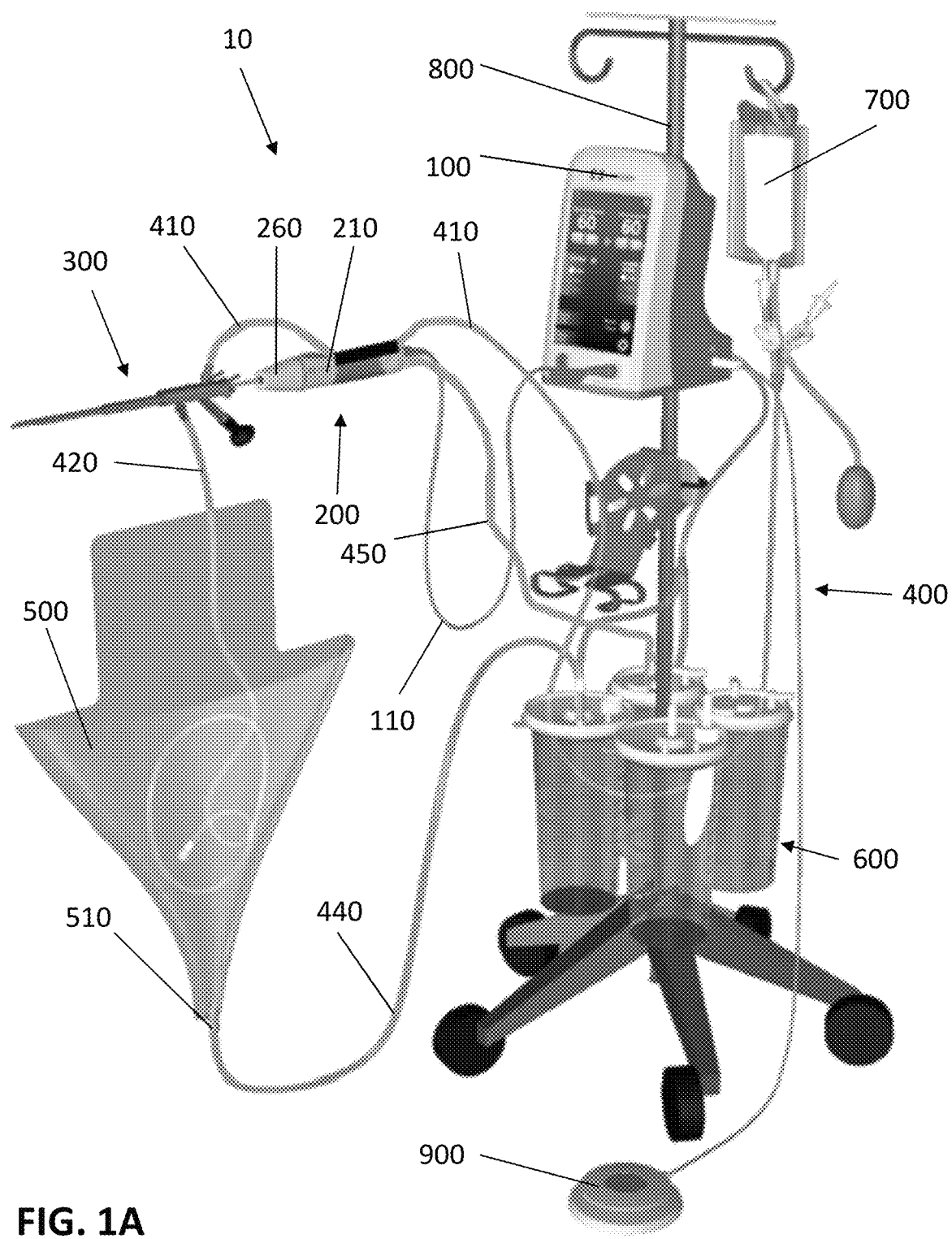
FIG. 1A is a perspective view of a surgical system provided in accordance with aspects of the present disclosure.

Referring to FIG. 1A, a surgical system provided in accordance with the present disclosure is shown generally identified by reference numeral 10. Surgical system 10 generally includes a control console 100, a surgical instrument 200 including a handpiece 210 and an end effector assembly 260 attachable to handpiece 210, an endoscope 300 (or other suitable fluid delivery device configured to deliver fluid into an internal surgical site), connection tubing 400, a fluid collection drape 500, one or more fluid collection canisters 600, a fluid bag 700 (or other suitable fluid source), a support stand 800, and a footswitch 900. Additional or alternative components of surgical system 10 are also contemplated, depending upon a particular purpose. Surgical system 10 may be configured for use in intrauterine hysteroscopic surgical procedures and/or other suitable procedures.

Control console 100 is configured to power and control surgical instrument 200, e.g., via a cable 110 connecting control console 100 with handpiece 210 of surgical instrument 200, and to perform fluid management with respect to the introduction of fluid through endoscope 300 into the surgical site and/or the withdrawal of fluid from the surgical site via surgical instrument 200 and/or endoscope 300. Although shown as an integrated unit contained within a single housing, it is understood that control console 100 may consist of plural separate units physically and/or operably connected to one another in any suitable manner.

With respect to powering and controlling surgical instrument 200, one or more microprocessors of the control console 100 controls a motor 230 within handpiece 210 of surgical instrument 200 to drive surgical instrument 200 according to appropriate speed and/or direction profiles and provides torque limits to protect surgical instrument 200 and the patient. The microprocessor(s) of control console 100 also directs communicates with surgical instrument 200, e.g., to identify surgical instrument 200, verify surgical instrument 200 is permitted to be used, obtain operational parameters and/or other information associated with surgical instrument 200, write use or other information to surgical instrument 200, etc.

With respect to fluid management, control console 100 may selectively operate one or more inflow pumps (not explicitly shown) disposed therein or connected thereto, one or more vacuum pumps (not explicitly shown) disposed therein or connected thereto, and/or any other suitable inflow and/or outflow pump(s). Control console 100, more specifically, may monitor fluid flow rate, fluid pressure, total fluid volume, fluid impedance, fluid deficit, etc., control the one or more pumps based thereon, and/or provide feedback regarding the same, e.g., display status information, output notifications and/or alarms, disable features, etc.

With additional reference to FIGS. 1B-3 and 6, surgical instrument 200, as noted above, includes a handpiece 210 and an end effector assembly 260 attachable to handpiece 210. Surgical instrument 200 may be, for example, a motor-driven tissue shaver, as described herein, although other suitable surgical instruments including motors or other heat-generating components such as, for example, battery packs, controllers, generators, etc., are also contemplated. Handpiece 210 of surgical instrument 200 generally includes an outer housing 220, a motor 230 disposed within outer housing 220, one or more activation buttons 240 (e.g., for activating and/or controlling settings of surgical instrument 200), and cable 110 which is configured to operably connect motor 230, activation buttons 240, and/or other electronics of handpiece 210 to control console 100. Motor 230 includes an output rotor 232 configured to provide a rotational output to drive end effector assembly 260, e.g., upon activation of motor 230. Handpiece 210 is described in greater detail below.

End effector assembly 260 of surgical instrument 200 includes a proximal hub 270 configured to releasably engage outer housing 220 of handpiece 210, an outer shaft 280 extending distally from proximal hub 270, and an inner assembly 290 including an inner cutting shaft 292 extending through outer shaft 280 and a drive assembly 294 disposed within proximal hub 270, operably engaged with inner cutting shaft 292, and configured to operable couple to output rotor 232 of motor 230 such that, in response to activation of motor 230 to drive rotation of output rotor 232, inner cutting shaft 292 is driven to rotate continuously, oscillate rotationally, and/or oscillate translationally relative to outer shaft 280 to cut tissue at the distal end of surgical instrument 200. Outer shaft 280 and/or inner cutting shaft 292 may define open distal ends and/or side windows towards the distal ends thereof to enable tissue to be drawn therein and cut by the motion of inner cutting shaft 292. More specifically, in aspects, inner cutting shaft 292 may include an open distal end and may define a cutting edge 296 surrounding the open distal end. Inner cutting shaft 292 may be configured to rotate and oscillate translationally relative to a side window 282 defined through outer shaft 280 towards the distal end thereof to cut tissue extending through side window 282. Suction may be applied through inner cutting shaft 292 to facilitate suctioning tissue through side window 282 for cutting and to facilitate the withdrawal of cut tissue, fluid, and debris from the surgical site through inner cutting shaft 292.

Referring back to FIGS. 1A and 1B, endoscope 300 includes an elongated distal body portion 310 configured for insertion into a surgical site, e.g., through the cervix and into the uterus, a proximal handle portion 320 configured for manipulation by an operator. Proximal handle portion 320 includes an inflow port 330, an outflow port 340, and an arm 350 that is configured to connect to an imaging device (e.g., a camera) to capture images received via a visualization mechanism, e.g., optics (not shown), extending through elongated body portion 310. Endoscope 300 further includes an inflow channel and an outflow channel defined through elongated body portion 310 and fluidly coupled with inflow port 330 and outflow port 340, respectively. An instrument channel defined through elongated body portion 310 and configured to receive an instrument therethrough such as, for example, surgical instrument 200, may be shared with the inflow channel or the outflow channel or may be a separate channel. As an alternative to endoscope 300, another suitable fluid delivery device (for receipt of surgical instrument 200 or separate therefrom) configured to deliver fluid into an internal surgical site may be utilized as part of system 10.

Connection tubing 400 includes inflow tubing 410; outflow tubing 420, 430, 440; and vacuum tubing 450. Each tubing 410-450 may include one or more segments of tube that may be connected with one another directly (via a suitable coupler) or indirectly (via suitable intermediate components). Inflow tubing 410 connects fluid bag 700 with inflow port 330 of endoscope 300 to enable the delivery of fluid from fluid bag 700 through the inflow channel of endoscope 300 and into a surgical site. Fluid may be delivered from fluid bag 700 into the internal surgical site via gravity, an inflow pump (not shown) connected between fluid bag 700 and endoscope 300, and/or via vacuum assist, e.g., via suction established through outflow tubing 420 and 430. Inflow tubing 410 forms at least a portion of a fluid inflow path from fluid bag 700 to endoscope 300. This fluid inflow path, as detailed below, is configured to thermally couple to one or more heat-generating components of surgical instrument 200 along at least a portion of the length of the fluid inflow path to simultaneously cool the heat-generating component(s) and warm the fluid flowing along the fluid inflow path by drawing heat away from the heat-generating components(s) and absorbing the heat with the fluid, respectively.

Outflow tubing 420 connects an outflow port 340 of endoscope 300 with the one or more fluid collection canisters 600 to enable the outflow of fluid from the surgical site, through endoscope 300, to the one or more fluid collection canisters 600. Outflow tubing 430 connects surgical instrument 200 with the one or more fluid collection canisters 600 to enable the removal of fluid, cut tissue, and debris from the surgical site through surgical instrument 200 and to the one or more fluid collection canisters 600. Outflow tubing 440 connects an outflow drain 510 of collection drape 500 with the one or more fluid collection canisters 600. Vacuum tubing 450 connects the one or more fluid collection canisters 600 with a vacuum pump (not shown) within control console 100 to establish suction through outflow tubing 420, 430, 440 to facilitate the outflow of fluid from the surgical site to the one or more fluid collection canisters 600.

Fluid collection drape 500 is configured to collect leakage fluid and return the same to the one or more fluid collection canisters 600 via outflow tubing 440 and drain 510 of fluid collection drape 500.

Fluid bag 700 (or other suitable fluid source) may hold any suitable fluid to be introduced into the surgical site such as, for example, saline, sorbitol, or glycine.

Support stand 800 is configured to support control console 100, collection canister(s) 600, and fluid bag 700 thereon.

Footswitch 900 may be configured to connect to control console 100 to act as an input device for actuating and/or controlling surgical instrument 200.

Figure 2:
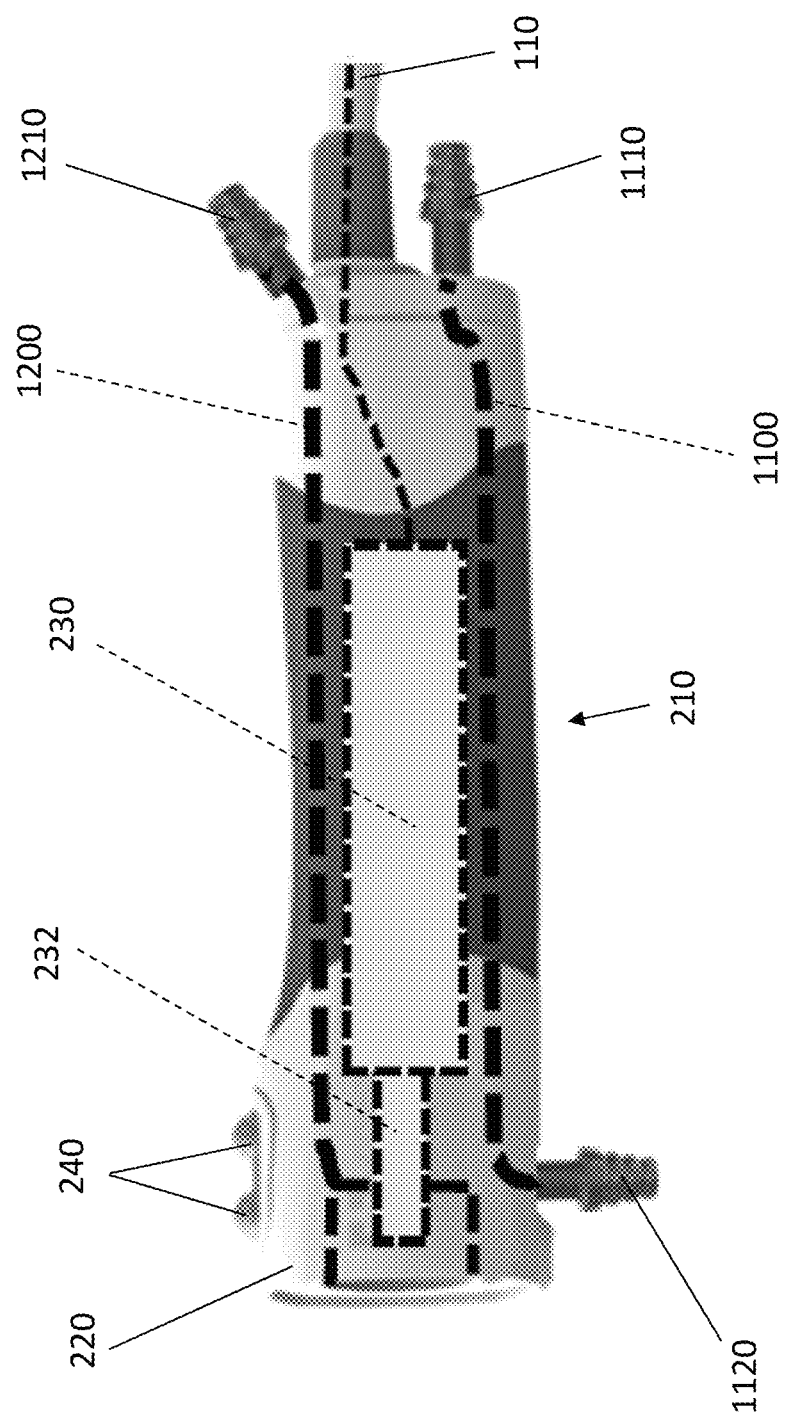
FIG. 2 is a side view of a handpiece of a surgical instrument configured for use with the surgical system of FIG. 1A in accordance with aspects of the present disclosure.
Figure 3:
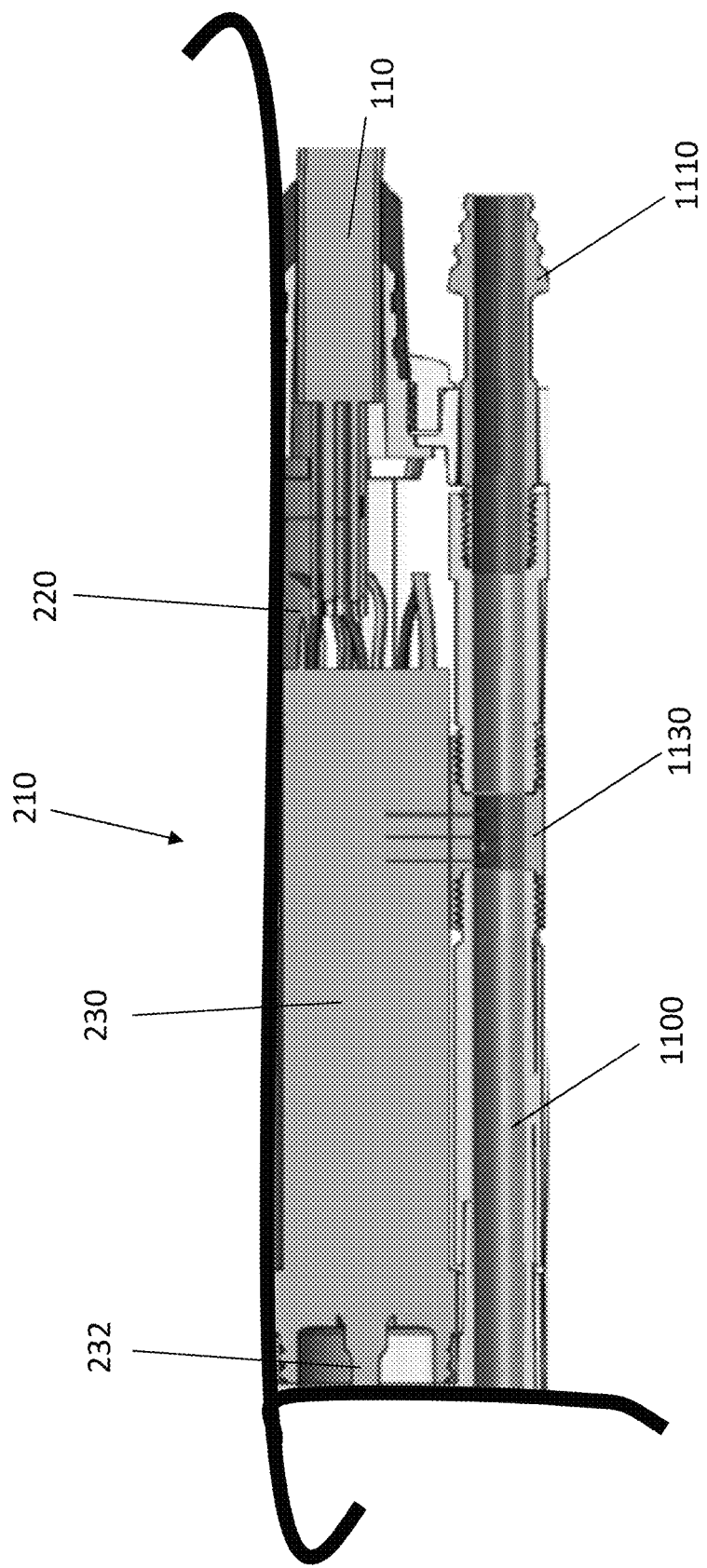
FIG. 3 is a longitudinal, cross-sectional view of a portion of the handpiece of FIG. 2.

Turning to FIGS. 2 and 3, in conjunction with FIG. 1A, inflow tubing 410, as noted above, forms at least a portion of the fluid inflow path from fluid bag 700 to endoscope 300. In order to thermally couple the fluid inflow path to motor 230 of handpiece 210 of surgical instrument 200 such that the fluid flowing along the fluid inflow path absorbs heat from motor 230 to cool motor 230 while simultaneously warming the fluid, surgical handpiece 210 defines an inflow lumen 1100 extending therethrough. First and second connection ports 1110, 1120 are disposed at opposite ends of inflow lumen 1100 in fluid communication with inflow lumen 1100 to enable segments of inflow tubing 410 to be connected to the input and output ends of inflow lumen 1100. More specifically, a first segment of inflow tubing 410 is connected between fluid bag 700 and first connection port 1110 while a second segment of inflow tubing 410 is connected between second connection port 1120 and inflow port 330 of endoscope 300 to establish the fluid inflow path from fluid bag 700 through endoscope 300 (via surgical instrument) and into the surgical site.

Inflow lumen 1100, more specifically, extends through outer housing 220 of handpiece 210 of surgical instrument 200. At least a portion of inflow lumen 1100 extends along at least a portion of motor 230 (in sufficient approximation relative thereto) to thermally couple inflow lumen 1100 with motor 230 to enable fluid flowing through inflow lumen 1100 to draw and absorb heat from motor 230, thereby cooling motor 230 and warming the fluid. Additionally or alternatively, a thermally conductive material(s) 1130 thermally couples motor 230 with at least a portion of inflow lumen 1100 to enable or facilitate the drawing of heat from motor 230 and absorption of heat by the fluid flowing through inflow lumen 1100 to thereby cool motor 230 and warm the fluid flowing through inflow lumen 1100.

Figure 1B:
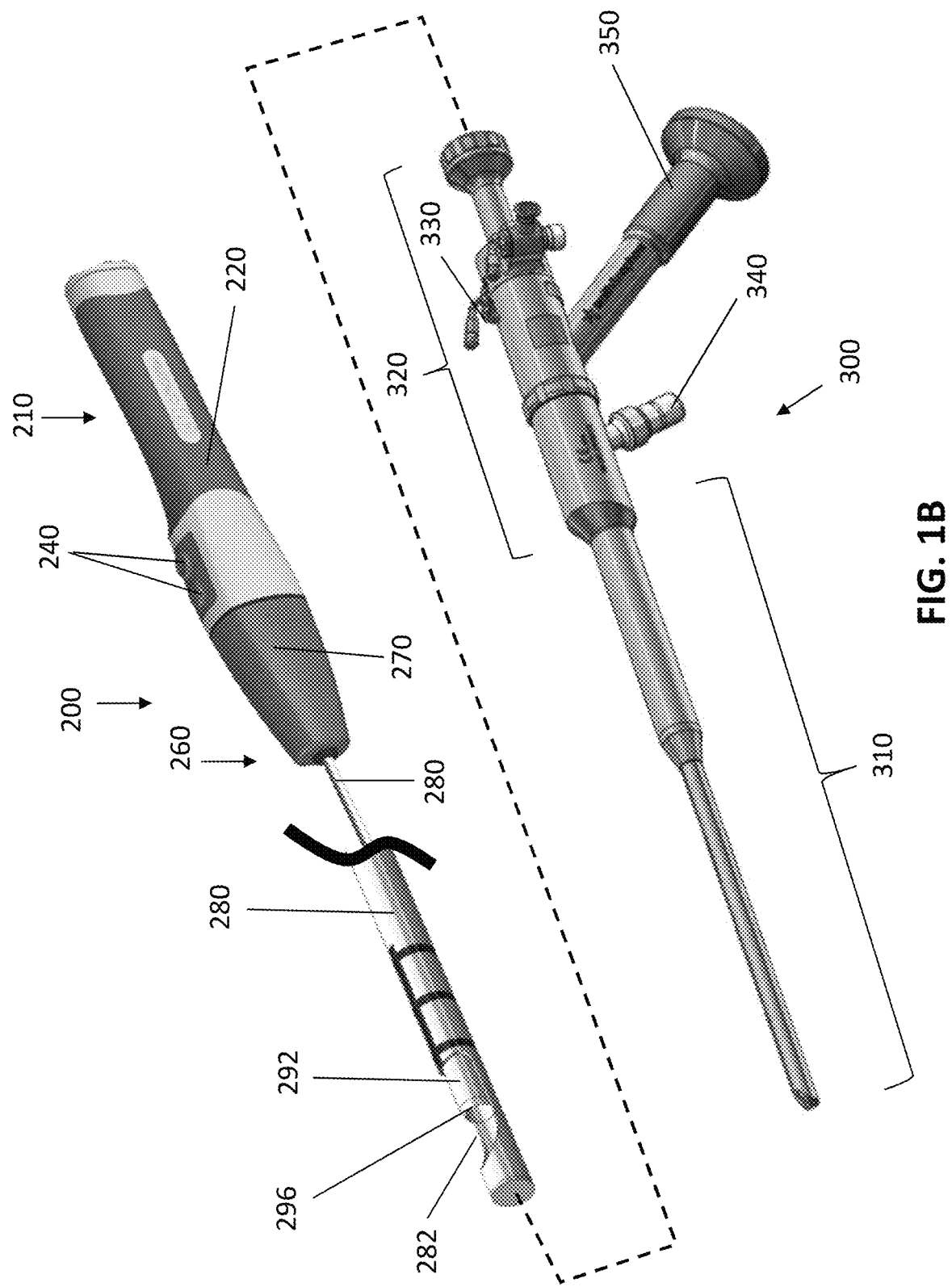
FIG. 1B is a perspective view of a surgical instrument and endoscope of the surgical system of FIG. 1A.

With additional reference to FIG. 1B, in aspects, handpiece 210 may further define an outflow lumen 1200 disposed in fluid communication with inner cutting shaft 292 of end effector assembly 260 when end effector assembly 260 is engaged with handpiece 210. Outflow lumen 1200 extends through outer housing 220 of handpiece 210 to an outflow connection port 1210 that connects to outflow tubing 430 to enable the removal of fluid, cut tissue, and debris from the surgical site through surgical instrument 200 and to the one or more fluid collection canisters 600. Outflow lumen 1200 may also be thermally coupled to motor 230 similarly as described above with respect to inflow lumen 1100 to further facilitate cooling of motor 230. Alternatively, motor 230 may be sufficiently cooled via the fluid flowing through inflow lumen 1100 and, thus, outflow lumen 1200 need not be thermally coupled to motor 230 or routed through handpiece 210.

Figure 4:
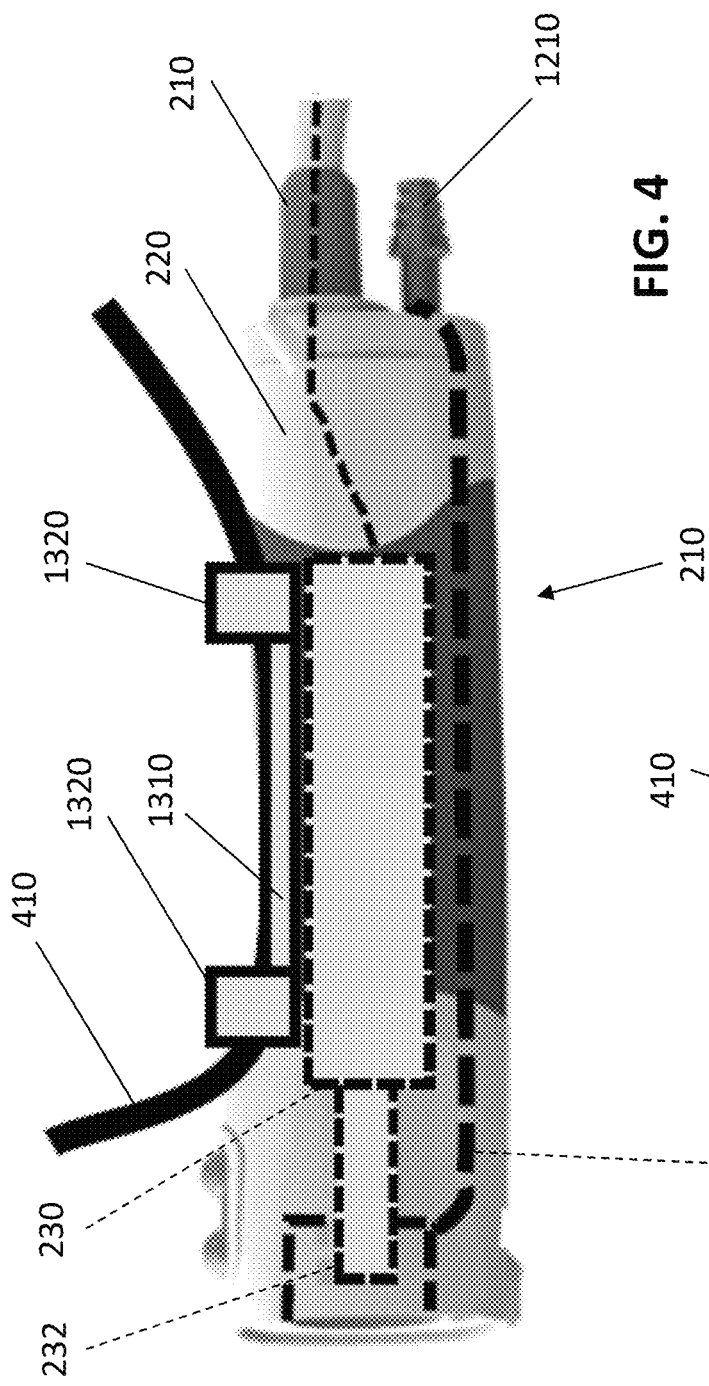
FIG. 4 is a side view of another handpiece of a surgical instrument configured for use with the surgical system of FIG. 1A in accordance with aspects of the present disclosure including inflow tubing operably coupled to the handpiece.
Figure 5:
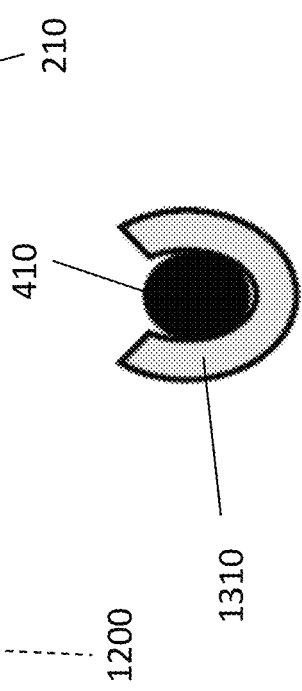
FIG. 5 is a transverse, cross-sectional view illustrating operable coupling of the inflow tubing with the handpiece of FIG. 4.

Turning to FIGS. 4 and 5, in order to thermally couple the fluid inflow path to motor 230 of handpiece 210 of surgical instrument 200 such that the fluid flowing along the fluid inflow path draws and absorbs heat from motor 230 to cool motor 230 while simultaneously warming the fluid, surgical handpiece 210 may be configured to releasably engage a portion of inflow tubing 410 such that the portion of inflow tubing 410 is thermally coupled with motor 230 to enable fluid flowing through inflow tubing 410 to absorb heat from motor 230, thereby cooling motor 230 and warming the fluid.

In order to facilitate the releasable engagement of inflow tubing 410 with handpiece 210, outer housing 220 of handpiece 210 may define a channel 1310 extending therealong and/or one or more retention elements 1320. Channel 1310 may be configured for press-fit receipt of inflow tubing 410 (see FIG. 5) to retain inflow tubing 410 in engagement with outer housing 220, or may receive inflow tubing 410 therein in any other suitable manner. Retention elements 1320 may include clips, latches, hooks, etc. to alternatively or additionally retain inflow tubing 410 in engagement with outer housing 220. Channel 1310 may be disposed in sufficient approximation with motor 230 to facilitate heat transfer from motor 230 to the fluid flowing through inflow tubing 410 and the warming of the fluid. Alternatively or additionally, a thermally conductive material (not explicitly shown) may be provided to thermally couple channel 1310 with motor 230 to enable heat to be drawn from motor 230 and absorbed by the fluid flowing through inflow tubing 410 to thereby cool motor 230 and simultaneously warm the fluid flowing through inflow tubing 410.

Similarly as detailed above, handpiece 210 may further define outflow lumen 1200 extending through outer housing 220 of handpiece 210 to outflow connection port 1210. Outflow lumen 1200 may also be thermally coupled to motor 230 similarly as described above to further facilitate cooling of motor 230. Alternatively, motor 230 may be sufficiently cooled via the fluid flowing through inflow tubing 410 within channel 1310 and, thus, outflow lumen 1200 need not be thermally coupled to motor 230 or routed through handpiece 210.

Figure 6:
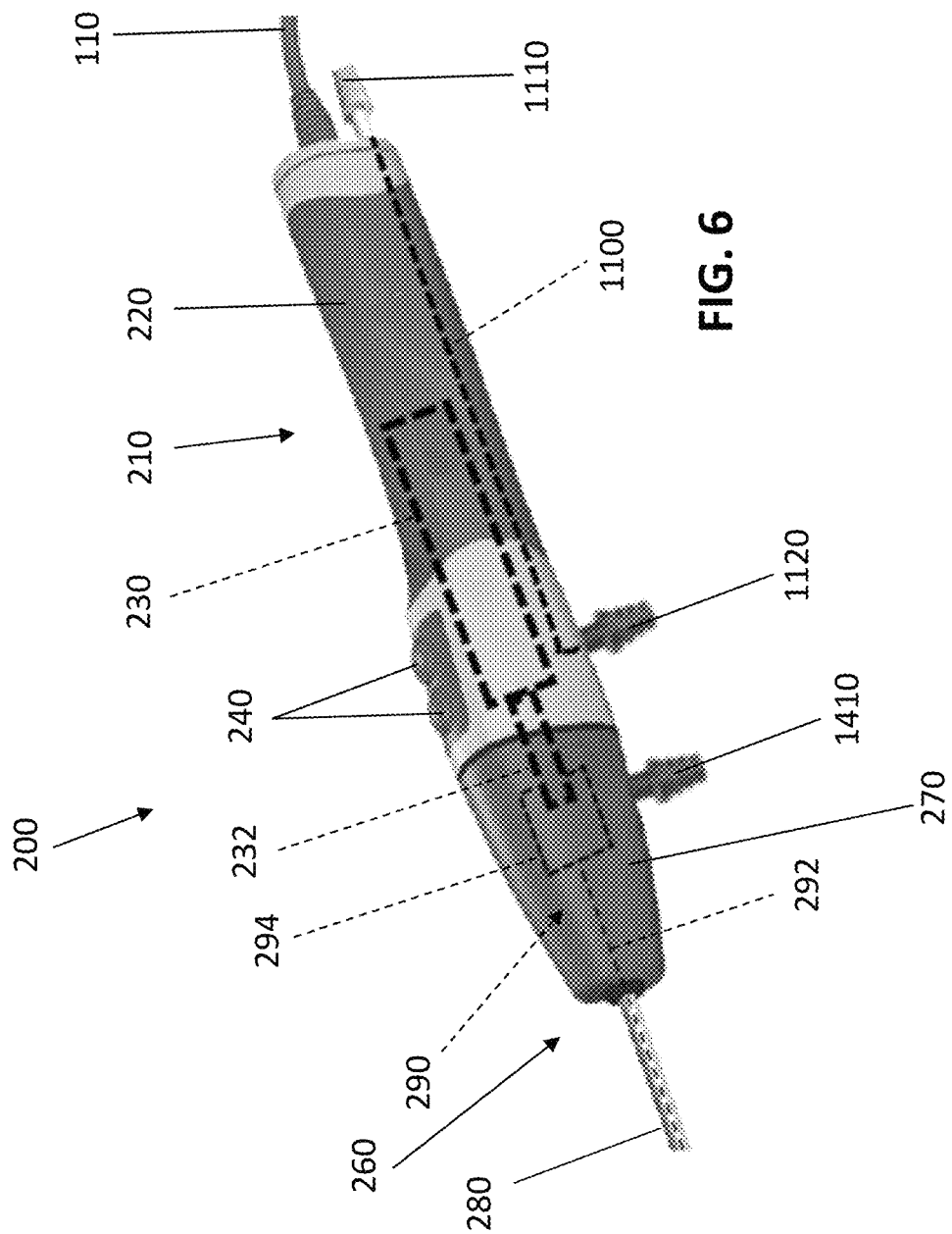
FIG. 6 is a perspective view of another surgical instrument configured for use with the surgical system of FIG. 1A in accordance with aspects of the present disclosure including a handpiece and an end effector assembly engaged with the handpiece.

Turning to FIG. 6, as noted above, the outflow fluid path through surgical instrument 200 need not extend through handpiece 210 (or be disposed in thermal communication with motor 230) in aspects where motor 230 is sufficiently cooled via the inflow fluid. That is, rather than extending the outflow fluid path through handpiece 210, end effector assembly 260 may include an outflow port 1410 disposed on proximal hub 270 thereof in fluid communication with the interior of proximal hub 270 and inner cutting shaft 292 such that outflow cut tissue, fluid, and debris are withdrawn from inner cutting shaft 292, through outflow port 1410 (bypassing handpiece 210) and outflow tubing 430 to the one or more collection canisters 600. In this manner, handpiece 210 can remain isolated from contact with outflow tissue, fluid, and debris, thus facilitating cleaning handpiece 210 for reuse.

While several aspects and features of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular configurations. Those skilled in the art will envision other modifications within the scope and spirit of the claims appended hereto.

What is claimed is:

1. A surgical system, comprising:
   a fluid-delivery device configured to deliver fluid to a surgical site;
   a surgical instrument including a handpiece and an end effector assembly releasably engaged with the handpiece, the handpiece including a heat-generating component and defining:
   a fluid outflow path thermally coupled to and extending along a first side of the heat-generating component from a distal portion of the handpiece, wherein the fluid outflow path is configured to fluidly couple to the end effector assembly, to a proximal portion of the handpiece, wherein the fluid outflow path is configured to connect to a vacuum source for withdrawing fluid from the surgical site; and
   a fluid inflow path thermally coupled to and extending along a second, opposite side of the heat-generating component from the proximal portion of the handpiece, wherein the fluid inflow path is configured to fluidly couple to a fluid source, to the distal portion of the handpiece, wherein the fluid inflow path is configured to fluidly couple to the fluid-delivery device to provide fluid to the fluid-delivery device for delivery to the surgical site,
   wherein the thermal coupling of the fluid inflow path with the heat-generating component of the handpiece simultaneously draws heat from the heat-generating component and warms fluid flowing distally along the fluid inflow path, wherein the thermal coupling of fluid outflow path with the heat-generating component of the handpiece simultaneously draws heat from the heat-generating component and warms fluid flowing proximally along the fluid outflow path, and wherein the fluid inflow path is fluidly isolated from the fluid outflow path and the end effector assembly.

2. The surgical system according to claim 1, wherein the fluid-delivery device is an endoscope.

3. The surgical system according to claim 2, wherein the endoscope is configured to receive a portion of the surgical instrument therethrough.

4. The surgical system according to claim 1, wherein the surgical instrument is a tissue shaver.

5. The surgical system according to claim 4, wherein the heat-generating component is a motor configured to drive a cutting shaft of the tissue shaver.

6. The surgical system according to claim 1, wherein an inflow lumen extending through the handpiece defines a portion of the fluid inflow path, and wherein the inflow lumen is thermally coupled to the heat-generating component.

7. The surgical system according to claim 1, wherein tubing engaged to the handpiece defines a portion of the fluid inflow path, and wherein the tubing is thermally coupled to the heat-generating component.

8. The surgical system according to claim 1, wherein the at least a portion of the fluid inflow path is thermally coupled to the heat-generating component of the surgical instrument via sufficient approximation-of the fluid inflow path with the heat-generating component.

9. The surgical system according to claim 1, wherein the at least a portion of the fluid inflow path is thermally coupled to the heat-generating component of the surgical instrument via a thermally conductive material connecting the fluid inflow path with the heat-generating component.

10. A method of surgery, comprising:
using a surgical instrument including a handpiece and an end effector assembly releasably engaged with the handpiece, wherein a heat-generating component of the handpiece of the surgical instrument generates heat during use of the surgical instrument, and wherein use of the surgical instrument includes withdrawing fluid from a surgical site along a fluid outflow path, at least a portion of the fluid outflow path thermally coupled to and extending proximally along a first side of the heat-generating component to simultaneously draw heat from the heat-generating component and warm fluid flowing proximally along the fluid outflow path; and
routing fluid along a fluid inflow path from a fluid source to the handpiece of the surgical instrument and from the handpiece of the surgical instrument to a surgical site such that the fluid inflow path is fluidly isolated from the fluid outflow path and the end effector assembly of the surgical instrument, wherein routing the fluid to the handpiece thermally couples at least a portion of the fluid inflow path to the heat-generating component of the handpiece with the at least a portion of the fluid outflow path extending distally along a second, opposite side of the heat-generating component to simultaneously draw heat from the heat-generating component and warm the fluid routed distally along the fluid inflow path from the handpiece of the surgical instrument to the surgical site.

11. The method according to claim 10, wherein using the surgical instrument includes inserting a portion of the end effector assembly of the surgical instrument into the surgical site.

12. The method according to claim 11, wherein using the surgical instrument further includes activating the surgical instrument to perform a surgical task at the surgical site.

13. The method according to claim 12, wherein the surgical task includes tissue cutting and removal, and wherein activating the surgical instrument includes activating a motor to drive a cutting shaft of the surgical instrument.

14. The method according to claim 13, wherein the motor is the heat-generating component.

15. The method according to claim 10, further comprising:
inserting an endoscope into the surgical site, wherein routing the fluid along the fluid inflow path from the fluid source to the surgical site includes routing the fluid through the endoscope.

16. The method according to claim 15, wherein using the surgical instrument includes inserting a portion of the end effector assembly of the surgical instrument through the endoscope and into the surgical site.

17. The method according to claim 10, wherein routing the fluid along the fluid inflow path from the fluid source to the surgical site includes routing the fluid through tubing engaged with the handpiece of the surgical instrument to thereby thermally couple the fluid inflow path with the heat-generating component.

18. The method according to claim 10, wherein the routing the fluid along the fluid inflow path from the fluid source to the surgical site includes routing the fluid through an internal lumen defined within the handpiece of the surgical instrument to thereby thermally couple the fluid inflow path with the heat-generating component.

19. The method according to claim 10, wherein the fluid inflow path is thermally coupled to the heat-generating component via at least one of: sufficient approximation of the fluid inflow path with the heat-generating component; or a thermally conductive material connecting the fluid inflow path with the heat-generating component.

* * * * *